Figure 1:
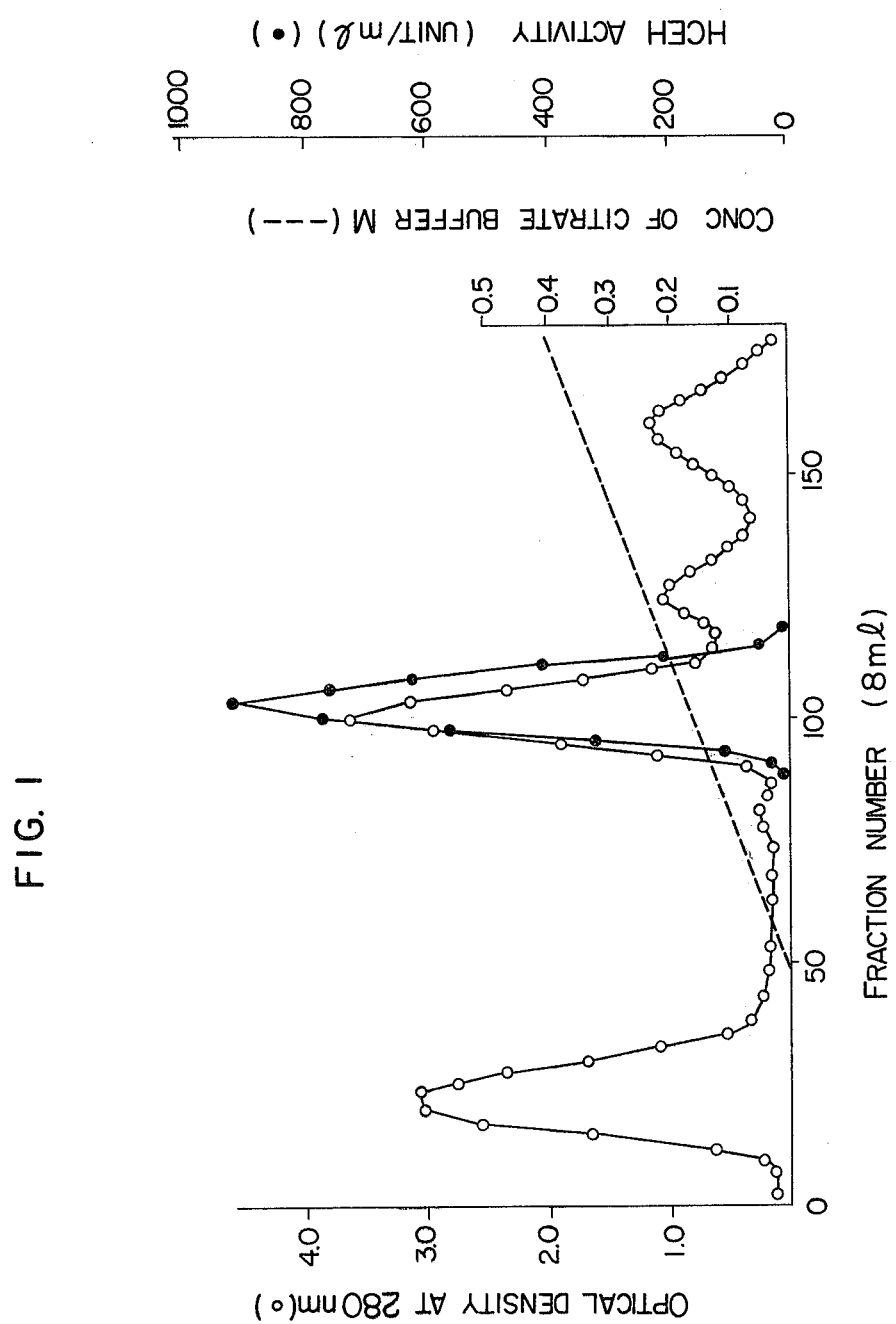

United States Patent [19]

Okamura et al.

[11] 4,426,448
[45] Jan. 17, 1984

[54] NOVEL HYDROXY-CINNAMIC ACID ESTER HYDROLASE AND PROCESS FOR PRODUCING SAME

[75] Inventors: Shigemichi Okamura, Noda; Masazumi Watanabe, Kashiwa, both of Japan

[73] Assignee: Kikkoman Corporation, Noda, Japan

[21] Appl. No.: 440,453

[22] Filed: Nov. 10, 1982

Related U.S. Application Data

[62] Division of Ser. No. 325,182, Nov. 27, 1981, Pat. No. 4,370,416.

[30] Foreign Application Priority Data

Dec. 8, 1980 [JP] Japan .................................. 55-172118

[51] Int. Cl.³ .......................... C12P 7/42; C12G 1/00; A23L 1/20
[52] U.S. Cl. ..................................... 435/146; 426/15; 426/45; 426/51
[58] Field of Search .................... 435/146; 426/15, 45, 426/51

[56] References Cited

PUBLICATIONS

Schobel et al. in Zeitschrift fur Naturforschung, vol. 35C, pp. 209–212 (Jan. 1980).

Merck Index 9th Edition (1976), pp. 272–273, entry 2121.

Iibuchi et al., Agr. and Biol. Chem. 31:513–518 (1967).

*Primary Examiner*—Lionel M. Shapiro
*Attorney, Agent, or Firm*—Schuyler, Banner, Birch, McKie & Beckett

[57] ABSTRACT

A novel hydroxy-cinnamic acid ester hydrolase can be obtained by cultivating, in a medium, a mold strain belonging to Genus Aspergillus or Genus Botrytis and having an ability to produce a hydroxy-cinnamic acid ester hydrolase specifically hydrolyzing the ester linkage of hydroxy-cinnamic acid ester substances represented by the following general formula:

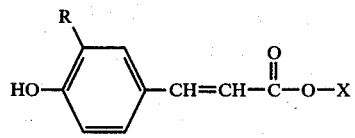

wherein R is hydrogen atom, hydroxyl group or methoxyl group and X is tartaric acid residue or quinic acid residue, followed by collecting the hydroxy-cinnamic acid ester hydrolase from the cultivated product.

2 Claims, 3 Drawing Figures

NOVEL HYDROXY-CINNAMIC ACID ESTER HYDROLASE AND PROCESS FOR PRODUCING SAME

This application is a division, of application Ser. No. 325,182, filed Nov. 27, 1981, now U.S. Pat. No. 4,370,416, issued Jan. 25, 1983.

This invention relates to a novel hydroxy-cinnamic acid ester hydrolase and to a process for producing a novel hydroxy-cinnamic acid ester hydrolase by the use of a mold fungus belonging to Genus Aspergillus or Genus Botrytis.

The novel hydroxy-cinnamic acid ester hydrolase (hereinafter, simply referred to as HCEH) obtainable by the process of this invention is a novel enzyme hydrolyzing the ester linkage of hydroxy-cinnamic acid ester substances represented by the following general formula:

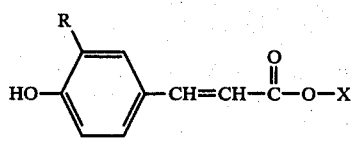

wherein R is hydrogen atom, hydroxyl group or methoxyl group and X is tartaric acid residue or quinic acid residue, such as p-coumaroyl tartaric acid, caffeoyl tartaric acid, feruloyl tartaric acid, 3-caffeoyl quinic acid and the like.

The present inventors conducted many studies on the polyphenol substances in fermented fruit drinks. As the result, it was found that a large quantity of hydroxy-cinnamic acid ester substances are present in fermented fruit drinks together with tannic acid, they give a bitter taste to the drinks, and particularly the hydroxy-cinnamic acid ester substances exercise an important influence as a substrate for the enzymatic browning.

As a method for removing the phenolic acid ester substances in fermented fruit drinks, the use of tannase which hydrolyzes the ester linkage of phenolic acid ester substances is hitherto well known, for example. However, the substrate of tannase is depside substance of gallic acid such as tannic acid, methyl gallate or the like, and tannase hardly or by no means exhibits a hydrolyzing action upon hydroxy-cinnamic acid ester substances.

The present inventors conducted earnest studies on the method for removing the hydroxy-cinnamic acid esters present in fermented fruit drinks to find that a novel HCEH capable of hydrolyzing the ester linkage of hydroxy-cinnamic acid ester substances can be obtained by cultivating a mold strain belonging to Genus Aspergillus or Genus Botrytis in the conventional solid or liquid media and that, if this novel HCEH is applied to materials containing a hydroxy-cinnamic acid ester substance such as fermented fruit drinks, a fermented fruit drink released in bitter taste, higher in quality and stable in color and gloss can be obtained. This invention was accomplished based on this finding.

It is an object of this invention to provide a novel hydroxy-cinnamic acid ester hydrolase and a process for producing said hydrolase.

Other objects and advantages of this invention will become apparent from the descriptions given below.

Figure 2:
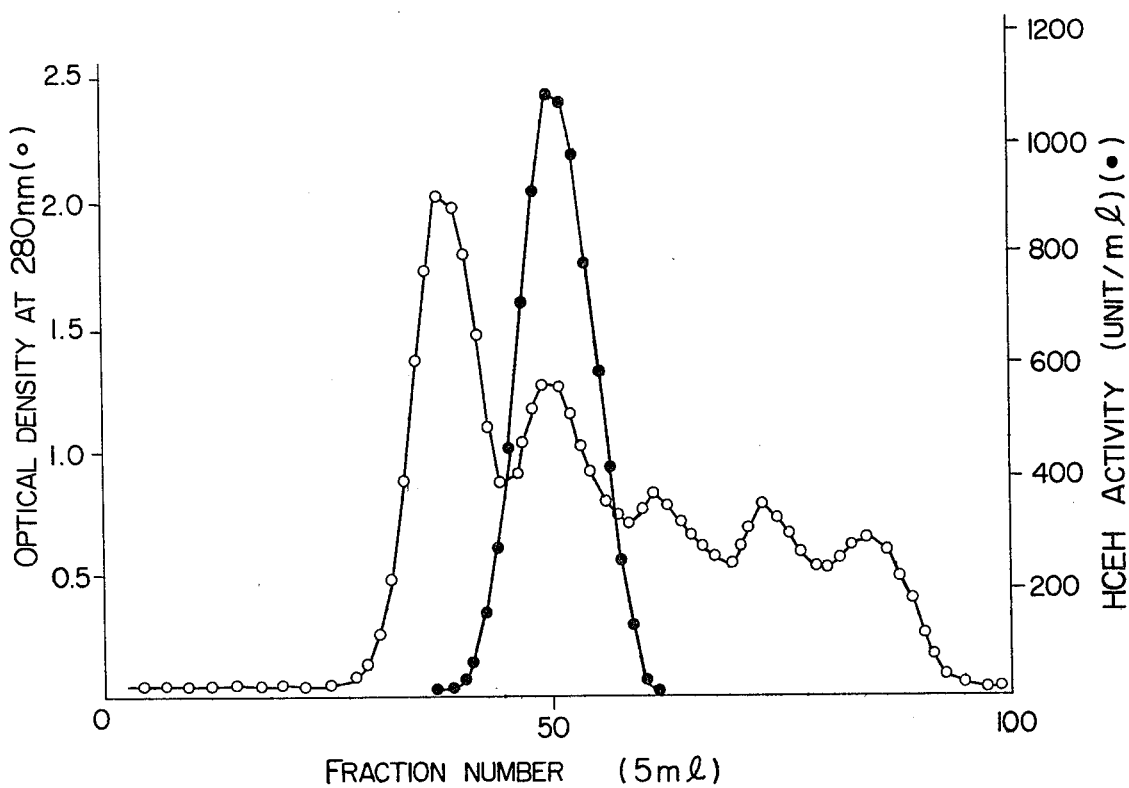
Figure 3:
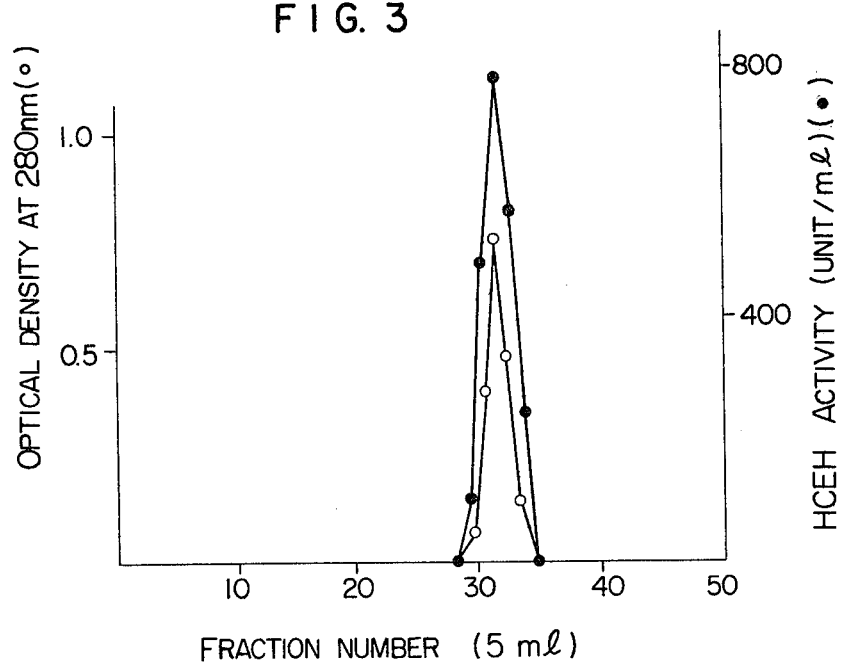

In the drawings attached, FIG. 1 is a column chromatogram of the enzyme of this invention obtained in Example 1 (mentioned later) on CM-Sephadex C-50; FIG. 2 is a column chromatogram of the enzyme of this invention obtained in Example 1 on Sephadex G-200; and FIG. 3 is a preparative disk electrophoresis chart of the enzyme of this invention obtained in Example 1.

According to this invention, there is provided a novel HCEH, as well as a process for producing a novel HCEH characterized by cultivating, in a medium, a mold strain belonging to Genus Aspergillus or Genus Botrytis and having an ability to produce a novel HCEH hydrolyzing the ester linkage of hydroxy-cinnamic acid ester substances represented by the following general formula:

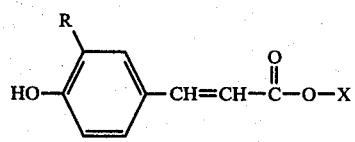

wherein R is hydrogen atom, hydroxyl group or methoxyl group and X is tartaric acid residue or quinic acid residue, followed by collecting the novel HCEH from the cultivated product.

First, the physico-chemical properties of the novel HCEH produced by the process of this invention will be mentioned.

(1) Action and substrate specificity

This enzyme acts upon the ester linkage of hydroxy-cinnamic acid ester substances represented by the following general formula:

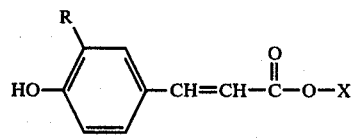

wherein R and X are as defined above, such as p-coumaroyl tartaric acid, caffeoyl tartaric acid, feruloyl tartaric acid, 3-caffeoyl quinic acid or the like to hydrolyze the ester linkage. It acts specifically upon the ester linkage of hydroxy-cinnamic acid ester substances and not upon other phenolic ester linkages (for example, gallic esters, benzoic esters and the like), so that it has no substantial tannic acid-decomposing activity.

(2) Optimum pH and stable pH range

Its optimum pH is 6.5, and its stable pH range is 3–7.5.

(3) Measurement of enzyme activity

In measuring the activity of the novel HCEH, 0.3 ml of a solution of the enzyme in 0.1 M phosphate buffer solution (pH 6.5) is added to 5 ml of a solution of commercial 3-caffeoyl quinic acid (manufactured by Tokyo Kasei Kogyo K.K.) in the same buffer solution as above having a concentration of 300 mg/liter, and reacted at 30° C. At predetermined time intervals, 0.5 ml of the reaction mixture is taken out, 10 ml of 80% aqueous methanol is added to stop the reaction, and optical density is measured at 340 nm. The activity is defined so that its one unit (U) is the quantity of the enzyme capable of hydrolyzing 1 nanomole of the substrate per one minute, and expressed by the value per 1 ml of the enzyme solution. The enzyme activity can be determined from the following equation:

$$U \text{ (unit)} = 6.01 \times 10^4 \times \frac{Et_1 - Et_2}{t_2 - t_1}$$

wherein:

$t_2-t_1$: reaction time (minute), $Et_1$: OD value at time $t_1$, $Et_2$: OD value at time $t_2$, provided that the value of $Et_1-Et_2$ should be 0.35 or less.

(4) The range of optimum action temperature

The optimum action temperature is in the range of 20°–60° C., and a temperature of about 45°–60° C. is most favorable.

(5) Inactivating pH and temperature conditions

It is completely inactivated by a heat-treatment at 70° C. for 10 minutes, and 80% of its activity remains after a treatment at 60° C. for 10 minutes.

It is inactivated at a pH value lower than 2 or higher than 9.

(6) Inhibition, activation and stabilization

It is inhibited by $Hg^{++}$, $Fe^{++}$, 8-hydroxyquinoline, p-CMB (p-chloromercury-benzoic acid), iodine and DFP (diisoproplyfluorophosphoric acid). There is no activator nor stabilizer particularly.

(7) Molecular weight

As measured according to the method of Andrews (P. Andrews: Biochem. J., Vol. 91, p. 222, 1960) by the use of Sephadex G-200 (manufactured by Pharmacia Fine Chemicals, Sweden), the molecular weight of this enzyme is 150,000 in 0.1 M citrate buffer solution of pH 5.0 at 4° C.

(8) It is an acidic protein having an isoelectric point of 4.8.

(9) Amino acid analyses (mole %)

Aspartic acid 12.4, threonine 6.2, serine 5.6, glutamic acid 8.7, proline 8.2, glycine 9.3, alanine 9.7, cystine 0.5, valine 7.6, methionine 1.0, isoleucine 4.2, leucine 6.7, tyrosine 6.8, phenylalanine 5.1, lysine 2.4, histidine 1.6, alginine 4.0, ammonia (13.6).

Hereunder, the process for producing the novel HCEH according to this invention will be mentioned concretely.

First, as the micro-organism used in this invention, the mold strains belonging to Genus Aspergillus or Genus Botrytis and having an ability to produce novel HCEH can be referred to. Concrete examples of the strain belonging to Genus Aspergillus include Aspergillus Sojae IAM 2678, Aspergillus niger IAM 3002, and Aspergillus japonicus No. 1744 ATCC 20236, and concrete examples of the strain belonging to Genus Botrytis include Botrytis cinerea FERM-P No. 1612 and Botrytis cinerea ATCC 20599.

However, the mold strains usable in the process of this invention are not limited to above, but all the mold fungi having an ability to produce the novel HCEH can be used.

The cultivation of the above-mentioned mold strains having an ability to produce the enzyme hydrolyzing the ester linkage of hydroxy-cinnamic acid ester substances is carried out by practising a solid culture or a liquid culture in the usual manner by using a medium usable for the cultivation of mold fungi.

As the nutrient source of the medium, those conventionally used in the cultivation of microorganisms can be used extensively.

That is, as the carbon source, any assimilable carbon compounds or materials containing them can be used, of which examples include wheat, bran, glucose, sucrose, starch, maltose, dextrin, glycerin, ethyl cinnamate, benzyl cinnamate, chlorogenic acid and the like. As the nitrogen source, any utilizable nitrogen compounds or materials containing them can be used, of which examples include soy bean flour, defatted soy bean flour, gluten, peptone, meat extract, casein, soy bean meal, corn steep liquor, ammonium sulfate, ammonium chloride and the like. Further, appropriate inorganic salts of phosphoric acid, potassium, magnesium, calcium or the like may be used adequately, and optionally various organic and inorganic substances necessary to the growth of fungi may be added to the medium.

In the case of solid culture, an appropriate starting material of solid medium such as bran is sprayed with water and sterilized at 120° C. for 30 minutes, after which cultivation is carried out at 30° C. for 3–5 days. An appropriate amount of water or buffer solution is added to the cultivated product of bran (koji) thus obtained, and extraction is carried out at room temperature for an appropriate period of time to obtain an extract solution. By further subjecting it to a treatment such as filtration with diatomaceous earth or centrifugation, a transparent extract solution can be obtained.

In the case of liquid culture, a nutrient medium prepared by appropriately combining the above-mentioned carbon source, nitrogen sources and inorganic salts, such as a medium comprising benzyl cinnamate, glucose, peptone, ammonium sulfate, yeast extract, $KH_2PO_4$ and the like, is adjusted to pH 5–7 and heat-sterilized in the usual manner, after which it is inoculated with seed fungi and cultivated. In this case, the cultivation can be practised by appropriate culture process such as standing culture, shaking culture, agitation culture, aeration culture and so on, among which aeration-agitation culture is preferable when the cultivation is carried out on a large scale.

Though the culture temperature may be changed in the range allowing the growth of said enzyme-producing fungi and the production of the enzyme, a particularly preferable temperature range is 25°–30° C.

Though the time period of cultivation varies depending on the fungi used and the form of cultivation, it is usually about 1–5 days. The cultivation may be ended by checking the time when the accumulation of produced enzyme reaches the maximum.

The culture product thus obtained in which the enzyme has been produced and accumulated is subjected to centrifugation or filtration with diatomaceous earth to obtain a culture filtrate. The extract solution or a culture filtrate thus obtained is subjected to salting out with ammonium sulfate or the like to obtain a precipitate, which is then dialyzed and freeze-dried to obtain a crude enzyme powder. Otherwise, a precipitate is prepared by the organic solvent precipitation method using alcohol or acetone, and it is freeze-dried to obtain a crude enzyme powder.

In preparing the enzyme precipitate from the extract solution by saturation with ammonium sulfate, the precipitate can be obtained at a 60–90% saturation with ammonium sulfate in the case of Aspergillus japonicus No. 1744 ATCC 20236, while it can be obtained at a 50–90% saturation with ammonium sulfate in the case of other strains. When the enzyme precipitate is prepared by the organic solvent precipitation method, the precipitate can be obtained at an acetone or alcohol concentration of 50–80%.

Said crude enzyme powder can be made into a purified enzyme either by a single means such as gel filtration using ion-exchange Sephadexes such as DEAE-Sephadex A-50, QAE-Sephadex A-50, CM-Sephadex or the like or Sephadexes such as Sephadex G-200 or the like (Sephadex is trademark and manufactured by Pharmacia Fine Chemicals, Sweden. The main structure of Sephadex is composed of dextran.), isoelectric point fractionation method using Ampholine (manufactured by LKB, Sweden), electrophoresis using acetate membrane, starch and acrylamide gel, isoelectric point precipitation method and the like or by appropriate combination of these means.

The novel HCEH obtained in this invention is easily distinguishable from tannase, the hitherto known tannic acid-hydrolyzing enzyme, by the following method. Thus, the tannase activity of an aqueous solution (500U) of purified novel HCEH having a 3-caffeoyl quinic acid-hydrolyzing action was measured by the method of Iibuchi et al. (Agr. Biol. Chem., Vol. 31, No. 5, 513–518, 1967). That is, 0.350% W/V of purified tannic acid was dissolved into 0.05 M citrate buffer solution (pH 5.5). One milliliter of the aqueous solution of purified HCEH was added to 4 ml of this substrate solution and kept at 30° C. After a predetermined period of time, 0.1 ml of the reacted solution was taken out, the reaction was stopped by adding 10 ml of 90% solution of ethanol thereto, and the optical density was measured at 310 nm. The tannase activity was defined as the amount of enzyme capable of hydrolyzing 1μ mole of tannic acid in one minute, which was calculated according to the following equation:

$$\text{Tannase activity } (U) = 114 \times \frac{Et_1 - Et_2}{t_2 - t_1}$$

wherein $Et_1$ and $Et_2$ are optical densities (OD) of the ethanolic solution after $t_1$ and $t_2$ minutes, respectively, at 310 nm.

When tannase activity of the purified novel HCEH was measured by the above-mentioned method, $Et_1 = Et_2$ held regardless of reaction time, so that tannase activity was not observed at all.

The novel HCEH and tannase can easily be separated into different fractions by the following method. Thus, a crude enzyme exhibiting both the activities of the novel HCEH and tannase is made into a solution in 0.01 M citrate buffer solution (pH 6.0) and then desalted by dialysis, column chromatography using Sephadex G-25 or ultrafiltration. After adjusting the crude enzyme protein solution thus obtained to a protein concentration of 2% (W/V) or less with 0.01 M citrate buffer solution (pH 6.0), it is subjected to column chromatography by the use of DEAE-Sephadex A-25 previously bufferized with 0.01 M citrate buffer solution (pH 6.0), provided that the resin is used in an amount of 100 ml or more per 1 g of protein. By using 0.01 M citrate buffer solution (pH 6.0) as a moving phase, the protein component not adsorbed on the resin is collected (fraction A). When elution of the protein has ended, it is started to let 0.2 M citrate buffer solution (pH 6.0) flow through the column. By this buffer solution, the protein component adsorbed on the resin is eluted (fraction B).

The HCEH activity and tannase activity of fraction A and fraction B are respectively measured by the above-mentioned methods. As the result, only HCEH activity is observed in fraction A and only tannase activity is observed in fraction B.

From these results, it is understandable that the HCEH enzyme obtained by this invention is an enzyme protein substance different from tannase which is the hitherto known phenolic ester-decomposing enzyme.

Hereunder are presented an experimental example in which caffeoyl tartaric acid, the hydroxy-cinnamic acid ester in wine, is hydrolyzed by the use of novel HCEH and an experimental example in which the degree of browning is given as a function of caffeoyl tartaric acid content.

EXPERIMENTAL EXAMPLE

Caffeoyl tartaric acid isolated from a wine made from Koshu grape by the method of V. L. Singleton et al. (J. Sci. Food Agric., 29, 403, 1978) was dissolved into 0.1 M citrate buffer solution (pH 4.5) so as to give a concentration of 500 mg/liter. 180U Of the novel HCEH obtained in this invention was added to 10 ml of this solution and reacted at 30° C. After 30 minutes, 1 hour, 1.5 hours and 2 hours, the enzyme reaction was stopped by heat-treating the solution at 70° C. for 10 minutes to obtain solutions having a caffeoyl tartaric acid concentration of 380 mg/liter, 260 mg/liter, 140 mg/liter and 30 mg/liter, respectively.

The quantitative analysis of caffeoyl tartaric acid was carried out by liquid chromatography using octadecyl silica as a separating resin [Agri. Biol. Chem., Vol. 45, No. 9, 2063–2070 (1981)].

Next, a crude enzyme solution of polyphenoloxidase previously prepared from the fruit juice of Koshu grade grape by the method of N. S. Dizik et al. (J. Fd. Sci., 35, 282, 1970) was added to the solutions obtained above in an amount of 5% and left standing at 30° C. for 1 hour, after which the degree of browning of the solutions at 430 nm was measured. The results are shown in Table 1.

TABLE 1

|  | Caffeoyl tartaric acid (mg/liter) | Degree of browning (ΔOD at 430 nm) |
|---|---|---|
| Control | 500 | 0.24 |
| Sample 1 | 380 | 0.18 |
| Sample 2 | 260 | 0.12 |
| Sample 3 | 140 | 0.06 |
| Sample 4 | 30 | 0.02 |

It is verified from Table 1 that the degree of browning decreases and the color and gloss become stabler as the concentration of caffeoyl tartaric acid decreases.

Next, 180U of the novel HCEH was added to a solution of caffeoyl tartaric acid prepared in the same manner as above, and reacted at 30° C. for 3 hours to decompose the caffeoyl tartaric acid completely. Then, after adjusting 1 liter of the reaction mixture to pH 2, caffeic acid was extracted with the same volume of solvent such as ether, ethyl acetate or the like. For example, caffeic acid was extracted by adding ethyl acetate, shaking the mixture, collecting the ethyl acetate phase and twice repeating this procedure on the residual aqueous solution, and the ethyl acetate phase thus obtained was concentrated by means of rotary evaporator to obtain 280 mg of caffeic acid. Determination of caffeic acid was carried out according to the method of Okamura and Watanabe [Agri. Biol. Chem., Vol. 45, No. 9, 2063-2070 (1981)]. The caffeic acid thus obtained is effectively usable as an antioxidant.

Next, 500 mg of caffeoyl tartaric acid and 500 mg of tannic acid were dissolved into 1 l of 0.1 M citrate buffer solution (pH 4.5). After acting the novel HCEH thereupon in the same manner as above, the enzyme reaction was stopped to obtain the solutions shown in Table 2. Upon these solutions, a crude enzyme of polyphenol-oxidase was reacted in the same manner as above. The results are shown in Table 2.

TABLE 2

|  | Caffeoyl tartaric acid (mg/liter) | Tannic acid (mg/liter) | Degree of browning (ΔOD at 430 nm) |
| --- | --- | --- | --- |
| Control | 500 | 500 | 0.27 |
| Sample 1 | 375 | 500 | 0.20 |
| Sample 2 | 255 | 500 | 0.15 |
| Sample 3 | 140 | 500 | 0.08 |
| Sample 4 | 30 | 500 | 0.05 |

Here, the activity of HCEH on various hydroxy-cinnamic acid ester substances and tannic acid was determined by measuring the quantity of their hydrolysis by means of liquid chromatography using 0.1 M phosphate buffer solution (pH 6.5). The results are shown in Table 3, where the activity is expressed as molar ratio of produced hydrolyzate.

TABLE 3

| Name of substance | Relative activity (%) |
| --- | --- |
| 3-Caffeoyl quinic acid | 100 |
| Caffeoyl tartaric acid | 69.8 |
| p-Coumaroyl tartaric acid | 78.3 |
| Tannic acid | 0 |

The novel HCEH obtained by the process of this invention is applicable to material containing hydroxy-cinnamic acid ester substances such as fruit juices, fermented fruit drinks, coffee drinks and the like. Particularly when it is applied to fermented fruit drinks in which tannic acid and hydroxy-cinnamic acid ester substances coexist, the hydroxy-cinnamic acid ester substances are specifically hydroylzed. Thus, the fruit drinks obtained are released in bitter taste and stable in color and gloss. Further it has been ascertained that, owing to the presence of tannic acid, the buffering action of tannic acid gives a mild feeling to the flavor of fermented fruit drinks and further an antifungal action to microorganisms can also be expected.

Next, the process of this invention will be explained concretely with reference to examples, which are presented in no limitative way.

EXAMPLE 1

200 g Of wheat bran was sprayed with 200 ml of water and cooked in an autoclave at 1 atmosphere for 30 minutes. Then, Aspergillus japonicus No. 1744 ATCC 20236 was inoculated thereon and cultivated at 30° C. for 4 days. 1000 ml Of water was added to the Koji thus obtained and stirred at room temperature for 2 hours, after which it was filtered with cotton cloth. Further, after adding 150 g of celite, it was again filtered. 520 g Of ammonium sulfate was added to 850 ml of the extract solution thus obtained to precipitate the enzyme. The precipitate was collected by centrifugation, dissolved into 0.01 M citrate buffer solution (pH 6.0), thoroughly dialyzed with a cellulose tubing against the same buffer solution and then subjected to column chromatography using DEAE-Sephadex A-25. Thus, the enzyme solution thoroughly dialyzed against 0.01 M citrate buffer solution was passed through DEAE-Sephadex A-b 25 equilibrated with 0.01 M citrate buffer solution (pH 6.0) to adsorb the impurity proteins. The enzyme protein solution not adsorbed by this procedure was dialyzed against 0.01 M citrate buffer solution (pH 4.0) and thereafter subjected to column chromatography using CM-Sephadex C-50. Thus, the enzyme solution was adsorbed on CM-Sephadex C-50 equilibrated with 0.01 M citrate buffer solution (pH 4.0), thoroughly washed and then eluted while continuously elevating the molar concentration of the buffer solution. The fractions eluted at buffer solution concentration ranging from 0.13 to 0.18 M having fraction numbers of 95–108, having a total volume of 112 ml, were collected (refer to FIG. 1 illustrating the column chromatogram of this enzyme with CM-Sephadex C-50). The combined fractions were dialyzed with a cellulose tubing against pure water and then freeze-dried. The dry product was dissolved into a small amount of 0.1 M citrate buffer solution (pH 5.0) and subjected to gel filtration using Sephadex G-200 column. The chromatogram was as shown in FIG. 2. The fractions exhibiting the activity of the novel HCEH were collected, freeze-dried and again subjected to column chromatography using Sephadex G-200. Thus, there was obtained 10.8 mg of a purified enzyme which contained no enzymes other than the novel HCEH at all and was homogeneous both ultracentrifugally and electrophoretically.

FIG. 3 illustrates the preparative disk electrophoresis chart of the purified enzyme obtained in the above-mentioned manner.

EXAMPLE 2

100 ml Of a liquid medium comprising 0.2% of $NH_4Cl$, 0.3% of $KH_2PO_4$, 0.01% of $MgSO_4.7H_2O$ and 20% of benzyl cinnamate (pH 6.0) was introduced into Sakaguchi flask having a capacity of 500 ml and cooked at 1 atmosphere for 15 minutes. Then, Aspergillus niger IAM 3002 was inoculated and subjected to shaking culture at 25° C. for 12 days with an amplitude of 10 cm at a speed of 140 r.p.m. After adding 300 g of celite to 2 liters of the culture fluid thus obtained, it was filtered.

The filtrate was concentrated to 100 ml by ultrafiltration (fractionated molecular weight: 10,000) and thoroughly dialyzed with a cellulose tubing against 0.01 M citrate buffer solution (pH 3.5), after which the insoluble matter was removed by centrifugation. The supernatant was subjected to column chromatography by adsorbing it on an SP-Sephadex C-50 column (1.9×30 cm) beforehand equilibrated with 0.01 M citrate buffer solution (pH 3.5), thoroughly washing the column and then eluting it while continuously elevating the concentration of the buffer solution. From the eluate, the fractions exhibiting the activity of the novel HCEH were taken out and combined. The fraction was dialyzed with a cellulose tubing against 0.01 M phosphate buffer solution (pH 7.5) and then subjected to column chromatography by adsorbing the novel HCEH on a DEAE-Sephadex A-50 column (1×25 cm) equilibrated with the same buffer solution and continuously elevating the concentration of the buffer solution. The fractions exhibiting the activity of the novel HCEH were collected and combined, dialyzed against water, and then freeze-dried. The powder thus obtained was dissolved into a small amount of 0.1 M phosphate buffer solution (pH 6.5), adsorbed on Sephadex G-200 equilibrated with the same buffer solution and subjected to column chromatography using the same buffer solution.

The novel HCEH thus obtained was uniform with respect to protein.

Total protein quantity (mg), total activity (units), specific activity (units/mg) and some others found at various stages of the above-mentioned purification process are shown in Table 4. The total protein quantity (mg) was measured according to J. Biol. Chem., 193, 265–275 (1951).

TABLE 4

|  | Amount of liquid (ml) | Total protein quanity (mg) | Total activity (units) | Specific activity (units/mg) | Yield (%) |
| --- | --- | --- | --- | --- | --- |
| Culture filtrate | 2,000 | 420 | 61,000 | 145 | 100 |
| Concentrated filtrate of ultrafiltration | 100 | 380 | 58,000 | 153 | 95 |
| Novel HCEH fraction eluted from SP-Sephadex | 83 | 120 | 41,000 | 342 | 67.2 |
| Novel HCEH fraction eluted from DEAE-Sephadex | 78 | 34 | 29,000 | 853 | 47.5 |
| Novel HCEH fraction eluted from Sephadex G-200 | 42 | 20 | 18,000 | 900 | 29.5 |

EXAMPLE 3

100 g Of wheat bran was sprayed with 80 ml of water containing 5 g of suspended ethyl cinnamate, and sterilized in an autoclave at 1 atmosphere for 30 minutes. Then Botrytis cinerea ATCC 20599 was inoculated thereon and cultivated at 28° C. for 10 days.

600 ml Of service water was added to the Koji thus obtained, stirred at room temperature for 2 hours and then filtered to obtain an extract solution. To the extract solution was added 3 times its quantity of ethanol while cooling the solution, and the resulting mixture was left standing overnight at 4° C. The resulting precipitate was collected by centrifugation and vacuum-dried to obtain 38 g of a crude enzyme. The crude enzyme was dissolved into 400 ml of water, the insoluble matter was removed by centrifugation, and then 237 g of ammonium sulfate was added to the supernatant. The resulting precipitate was collected by centrifugation, dissolved into 60 ml of water and subjected to column chromatography using a Sephadex G-25 column (1.9×120 cm) to remove salts from the solution. This solution was dialyzed with a cellulose tubing against 0.01 M citrate buffer solution (pH 4.2) and subjected to column chromatography using CM-Sephadex C-50 column equilibrated with the same buffer solution. Thus, the chromatography was carried out by adsorbing the enzyme on CM-Sephadex C-50, washing the column with the same buffer solution and then carrying out elution while continuously elevating the concentration of the buffer solution. The fraction exhibiting the activity of novel HCEH was again subjected to chromatography in the same manner as above while continuously elevating the concentration of citrate buffer solution from the start value of 0.01 M. The fraction exhibiting the activity of novel HCEH was dialyzed with a cellulose tubing against 0.05 M citrate buffer solution (pH 6.0) and then subjected to column chromatography using DEAE-Cellulose column equilibrated with the same buffer solution to adsorb impurities on DEAE-Cellulose. The eluted fraction exhibiting the activity of HCEH was dialyzed with a cellulose tubing against 0.1 M citrate buffer solution (pH 6.0), concentrated by means of ultrafiltration (fractionated molecular weight: 50,000) and subjected to column chromatography using a Sephadex G-200 column equilibrated with 0.1 M citrate buffer solution (pH 6.0) to obtain a novel HCEH.

Total protein quantity, total activity, specific activity, yield and some others at various stages of the above-mentioned purification process are shown in Table 5.

TABLE 5

|  | Amount of liquid (ml) | Total protein quantity (mg) | Total activity (units) | Specific activity (units/mg) | Yield (%) |
| --- | --- | --- | --- | --- | --- |
| Crude extract solution | 560 | 3,180 | 78,000 | 24.5 | 100 |
| Ethanol-precipitated fraction | 400 | 1,520 | 51,000 | 33.6 | 65 |
| 0.8-saturation ammonium sulfate-precipitated fraction | 60 | 930 | 45,000 | 48.4 | 58 |
| Novel HCEH fraction eluted from 1st. CM-Sephadex | 82 | 230 | 36,000 | 156 | 46 |
| Novel HCEH fraction eluted from 2nd. CM-Sephadex | 70 | 140 | 31,000 | 221 | 40 |
| Novel HCEH fraction eluted from DEAE-Cellulose | 95 | 75 | 27,000 | 360 | 35 |
| Novel HCEH fraction eluted from Sephadex G-200 | 45 | 20 | 19,000 | 950 | 24 |

What is claimed is:

1. An enzymic process for the production of caffeic acid comprising:
   (a) adding an enzyme to a material containing at least one compound selected from the group consisting of caffeoyl tartaric acid and 3-caffeoyl quinic acid, said enzyme being a hydroxy-cinnamic acid ester hydrolase characterized by the following properties:
      (i) the ability to specifically hydrolyze the ester linkage of hydroxy-cinnamic acid ester substances represented by the following formula:

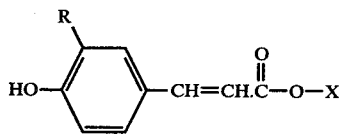

wherein R is selected from the group consisting of a hydrogen atom, a hydroxyl group and a methoxyl group, and X is selected from the group consisting of tartaric acid residue or quinic acid residue;

(ii) the lack of substantial tannic acid-decomposing activity;

(iii) an optimum pH for said hydrolase activity of about 6.5, and a stable pH range of from about 3 to about 7.5;

(iv) a loss of said hydrolase activity when heat-treated at 70° C. for 10 minutes and a maintenance of about 80% of said hydrolase activity when heat-treated at 60° C. for 10 minutes;

(v) inhibition by $Hg^{++}$, $Fe^{++}$, 8-hydroxyquinoline, iodine or diisopropylfluorophosphoric acid;

(vi) a molecular weight of about 150,000 as measured at 4° C. in a 0.1 M citrate buffer solution having a pH value of about 5.0; and (vii) an acidic protein with an isoelectric point of about PI 4.8, and (b) hydrolyzing the ester linkage of said compound with said enzyme to produce caffeic acid.

2. An enzymic process according to claim 1, wherein said material is must, wine or coffee.

* * * * *